US010843153B2

(12) United States Patent
Wang et al.

(10) Patent No.: US 10,843,153 B2
(45) Date of Patent: Nov. 24, 2020

(54) TWO-DIMENSIONAL NANOMATERIAL DISPERSANT, PREPARATION METHOD OF TWO-DIMENSIONAL NANOMATERIAL BY LIQUID PHASE EXFOLIATION, AND USE THEREOF

(71) Applicant: Ningbo Institute of Materials Technology & Engineering, Chinese Academy of Sciences, Ningbo (CN)

(72) Inventors: Liping Wang, Ningbo (CN); Jia Chen, Ningbo (CN); Mingjun Cui, Ningbo (CN); Cheng Chen, Ningbo (CN); Shihui Qiu, Ningbo (CN); Haichao Zhao, Ningbo (CN)

(73) Assignee: Ningbo Institute of Materials Technology & Engineering, Chinese Academy of Sciences, Ningbo (CN)

( * ) Notice: Subject to any disclaimer, the term of this patent is extended or adjusted under 35 U.S.C. 154(b) by 102 days.

(21) Appl. No.: 16/300,273

(22) PCT Filed: Oct. 8, 2016

(86) PCT No.: PCT/CN2016/101469
§ 371 (c)(1),
(2) Date: Nov. 9, 2018

(87) PCT Pub. No.: WO2017/193532
PCT Pub. Date: Nov. 16, 2017

(65) Prior Publication Data

US 2019/0143286 A1 May 16, 2019

(30) Foreign Application Priority Data

May 11, 2016 (CN) .......................... 2016 1 0310453
May 11, 2016 (CN) .......................... 2016 1 0310516
May 11, 2016 (CN) .......................... 2016 1 0311073
May 11, 2016 (CN) .......................... 2016 1 0312440
May 11, 2016 (CN) .......................... 2016 1 0315780

(51) Int. Cl.

| | |
|---|---|
| ***C01G 39/06*** | (2006.01) |
| ***B01F 17/00*** | (2006.01) |
| ***C01B 21/064*** | (2006.01) |
| ***C07C 233/44*** | (2006.01) |
| ***C07C 233/43*** | (2006.01) |
| *B82Y 30/00* | (2011.01) |
| *B82Y 40/00* | (2011.01) |

(52) U.S. Cl.
CPC ........ *B01F 17/0085* (2013.01); *B01F 17/005* (2013.01); *B01F 17/0007* (2013.01); *B01F 17/0042* (2013.01); *C01B 21/064* (2013.01); *C01B 21/0648* (2013.01); *C01G 39/06* (2013.01); *C07C 233/43* (2013.01); *C07C 233/44* (2013.01); *B82Y 30/00* (2013.01); *B82Y 40/00* (2013.01); *C01P 2004/03* (2013.01); *C01P 2004/04* (2013.01); *C01P 2004/24* (2013.01); *C01P 2006/22* (2013.01)

(58) Field of Classification Search
CPC ... C01B 21/064; C01B 21/0648; C01G 39/06; C07C 233/43; C07C 233/44; B01F 17/0085; B01F 17/0042; B01F 17/005
USPC .......................................................... 523/205
See application file for complete search history.

(56) References Cited

U.S. PATENT DOCUMENTS 10,421,875 B2 * 9/2019 Casiraghi ................. B05D 7/24
2016/0032062 A1 * 2/2016 Clauss ................... C08K 3/042
523/468

OTHER PUBLICATIONS

English translation of CN 103254429 (Year: 2013).*

* cited by examiner

*Primary Examiner* — Hannah J Pak
(74) *Attorney, Agent, or Firm* — Wang Law Firm, Inc.

(57) ABSTRACT

The present invention discloses a two-dimensional nanomaterial dispersant, a preparation method of a two-dimensional nanomaterial by liquid phase exfoliation, and use thereof. The present invention utilizes a readily synthesizable and inexpensive oligoaniline, oligoaniline derivative, polyaniline conducting polymer or the like as a dispersant of a two-dimensional nanomaterial, such as a boron nitride nanosheet or a molybdenum disulfide nanosheet, simply mixes the dispersant with boron nitride or molybdenum disulfide in a dispersion medium, such as water, an organic solvent, or a polymer resin, and can significantly improve dispersity and dispersion stability of the two-dimensional nanomaterial in the dispersion medium by a physical interaction therebetween; and can also obtain the two-dimensional nanomaterial in the dispersant by a simple liquid phase exfoliation method, which is an environment friendly and efficient process with simple operations without impairing the physical structure and chemical properties of the two-dimensional nanomaterial, and facilitates large-scale implementation.

13 Claims, 4 Drawing Sheets

TWO-DIMENSIONAL NANOMATERIAL DISPERSANT, PREPARATION METHOD OF TWO-DIMENSIONAL NANOMATERIAL BY LIQUID PHASE EXFOLIATION, AND USE THEREOF

TECHNICAL FIELD

The present invention specifically relates to a liquid phase exfoliation method of a two-dimensional nanomaterial, a two-dimensional nanomaterial dispersant, and a preparation method of a two-dimensional nanomaterial dispersoid, and a redispersible two-dimensional nanomaterial powder by a physical approach.

BACKGROUND

The two-dimensional nanomaterial generally has excellent physical and chemical properties, and has broad application prospects. For example, a boron nitride nanosheet, as a graphene two-dimensional nanomaterial, has good thermal conductivity, dielectricity, chemical stability, wear resistance, and the like. For another example, a molybdenum disulfide nanosheet, as a layered semiconductor material, has excellent performances in many fields, such as lubrication, ion exchange, adsorption, conduction, separation, and catalysis. However, limited to properties of such two-dimensional nanomaterials, it is difficult to achieve mass preparation of such two-dimensional nanomaterials at present.

For example, the boron nitride nanosheet tends to be agglomerated because of strong ion interaction between sheet layers, enabling it to tend to agglomerate and have limited solubility in an ordinary solvent, thus limiting its use to a large extent. A common preparation method of the two-dimensional boron nitride nanosheet mainly includes a "bottom-up" synthesis method and a "top-down" exfoliation method. The "bottom-up" synthesis method is mainly the chemical vapor deposition (CVD) method, which suffers from high preparation costs, is difficult to be controlled, and is difficult to achieve large-scale production. The "top-down" exfoliation method realizes exfoliation of the two-dimensional layered nanosheets mainly by resisting strong ionic bond interaction between boron nitride nanosheets in various ways. At present, the exfoliation method mainly includes a mechanical exfoliation method (such as a tape exfoliation method, a ball milling method, and a fluid exfoliation method) and a chemical exfoliation method (mainly including a liquid phase exfoliation method, a chemical function method, an ion insertion exfoliation method, and the like). However, the existing preparation methods of the boron nitride nanosheet generally have the defects, such as difficult operations, high costs, and difficult large-scale implementation, the resulting boron nitride nanosheet product has unstable quality, and it is also very difficult to obtain a few-layer or monolayer boron nitride nanosheet having a single sheet layer.

For another example, molybdenum disulfide sheet layers bind by a weak van der Waals force, and tend to twist and agglomerate under the external influence, thereby resulting in limited dispersion in a conventional solvent, and tending to agglomerate and precipitate. This limits its use to a large extent. In order to obtain a two-dimensional molybdenum disulfide nanomaterial, many solutions have been proposed by the industrial circle. For example, some researchers can exfoliate molybdenum disulfide in an organic solvent and form a molybdenum disulfide nanosheet by stirring or ultrasonic processing of molybdenum disulfide in an oxidant-containing mixed solvent. For example, some other researchers have obtained a mixed solution by dissolving an amphipathic surfactant in an organic solvent, and then ultrasonic processing in a water bath; then obtained a solid, i.e., the exfoliated two-dimensional layered nanomaterial, by adding a molybdenum disulfide powder to a mixed solution, ultrasonically processing and centrifuging the resulting solution, removing the supernatant, collecting the precipitate, and drying the precipitate. For another example, some researchers have achieved stable dispersion of $MoS_2$ sheet layers in water by inserting lithium between $MoS_2$ layers, and by ultrasound, but the process is complex, thereby limiting its use. For still another example, some researchers have reported that $MoS_2$ exfoliation can be achieved in a mixed solvent of ethanol and water at a certain ratio, but the dispersion concentration is very low, and is only 0.018 mg/mL. Some other researchers have also achieved stable dispersion of molybdenum disulfide in a water solution by auxiliary milling and acoustic degradation of N-methylpyrrolidone, and by changing the milling time and the milling-acoustic degradation time. However, the above preparation methods of the molybdenum disulfide nanosheet generally have the defects, such as difficult operations, and difficult large-scale implementation, and the quality of the obtained molybdenum disulfide nanosheet product is not stable.

SUMMARY

A main object of the present disclosure is to provide a two-dimensional nanomaterial dispersant, a preparation method of the two-dimensional nanomaterial by liquid phase exfoliation, and use thereof, to overcome the disadvantages of the existing technologies.

In order to achieve the object of the disclosure, the technical solution employed in the present disclosure includes:

A first aspect of an embodiment of the present invention provides a two-dimensional nanomaterial dispersant, which includes any one or a combination of two or more of an oligoaniline, an oligoaniline derivative, or a polyaniline conducting polymer, and is capable of binding to a two-dimensional nanomaterial by a physical action to enable the two-dimensional nanomaterial to be stably dispersed in a dispersion medium. The two-dimensional nanomaterial is selected from a two-dimensional boron nitride nanomaterial and a two-dimensional molybdenum disulfide nanomaterial.

Furthermore, the oligoaniline includes, but is not limited to, any one or a combination of two or more of an aniline trimer, an aniline tetramer, an aniline pentamer, or an aniline hexamer.

Furthermore, the oligoaniline derivative includes, but is not limited to, a derivative of any one of an aniline trimer, an aniline tetramer, an aniline pentamer, or an aniline hexamer.

Furthermore, the oligoaniline derivative includes a carboxyl end-capped oligoaniline derivative, an alkyl-substituted oligoaniline derivative, an oligoaniline binding to a functional group, or a small molecular compound containing an oligoaniline.

Preferably, the functional group includes, but is not limited to, any one or a combination of two or more of alkoxy, carboxyl, sulfo, or phosphoryl.

Preferably, the oligoaniline derivative is selected from, but is not limited to, an oligoaniline graft or block polymer.

Furthermore, the polyaniline conducting polymer includes, but is not limited to, any one or a combination of two or more of an eigenstate polyaniline, a doped polyaniline, a substituted polyaniline, an oil soluble polyaniline, or a water soluble polyaniline.

Preferably, the polyaniline conducting polymer includes a polyaniline conducting polymer having a structural unit represented by any one of chemical formulas (1)-(3):

(1)

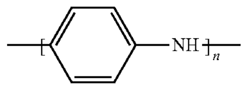

(2)

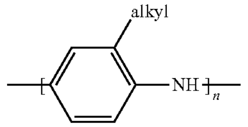

(3)

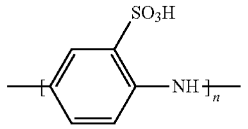

where, n=3-500, where the alkyl is an alkyl group.

Furthermore, a weight ratio of the dispersant to the two-dimensional nanomaterial is 0.1-10:1; and preferably, the weight ratio of the dispersant to the two-dimensional nanomaterial is 0.2-2:1. Preferably, the two-dimensional boron nitride nanomaterial or the two-dimensional molybdenum disulfide nanomaterial is selected from a nanosheet having a thickness of 1-20 nm.

Furthermore, the dispersion medium includes, but is not limited to, any one or a combination of two or more of water, an organic solvent, or a polymer resin.

A second aspect of an embodiment of the present invention provides a preparation method of a two-dimensional nanomaterial by liquid phase exfoliation, including: fully mixing a boron nitride powder or a molybdenum disulfide powder with a dispersant in a dispersion medium to form a stable dispersion of a two-dimensional nanomaterial. The dispersant is selected from any one of the two-dimensional nanomaterial dispersants.

Furthermore, the two-dimensional nanomaterial is selected from a two-dimensional boron nitride nanomaterial and a two-dimensional molybdenum disulfide nanomaterial.

Furthermore, the dispersion medium includes, but is not limited to, any one or a combination of two or more of water, an organic solvent, or a polymer resin.

Furthermore, the preparation method by liquid phase exfoliation further includes: centrifuging the stable dispersion of the two-dimensional nanomaterial to collect a complex of the two-dimensional nanomaterial and the dispersant.

A third aspect of an embodiment of the present invention provides a complex of a two-dimensional nanomaterial and a dispersant. The dispersant is selected from any one of the two-dimensional nanomaterial dispersants.

Furthermore, the two-dimensional nanomaterial is selected from a two-dimensional boron nitride nanomaterial and a two-dimensional molybdenum disulfide nanomaterial.

Furthermore, a weight ratio of the dispersant to the two-dimensional nanomaterial is 0.1-10:1, and preferably 0.2-2:1.

Furthermore, the two-dimensional boron nitride nanomaterial or the two-dimensional molybdenum disulfide nanomaterial is selected from a nanosheet having a thickness of 1-20 nm.

A fourth aspect of an embodiment of the present disclosure further provides a two-dimensional nanomaterial dispersoid, including: a dispersion medium; and a complex of any one of the two-dimensional nanomaterials and the dispersant dispersed in the dispersion medium.

Furthermore, the two-dimensional nanomaterial dispersoid is a fluid dispersoid, and preferably a liquid dispersoid or slurry.

Furthermore, the dispersion medium includes, but is not limited to, any one or a combination of two or more of water, an organic solvent, or a polymer resin.

Furthermore, the two-dimensional nanomaterial dispersoid includes a two-dimensional nanomaterial of less than 10 mg/mL.

Preferably, the two-dimensional nanomaterial dispersoid includes a two-dimensional nanomaterial of less than 0.1 mg/mL-5 mg/mL, 0.1 mg/mL-3 mg/mL, or 0.1 mg/mL-2.5 mg/mL.

Furthermore, the two-dimensional boron nitride nanomaterial or the two-dimensional molybdenum disulfide nanomaterial is selected from a nanosheet having a thickness of 1-20 nm.

A fifth aspect of an embodiment of the present invention provides a preparation method of a two-dimensional nanomaterial dispersoid, including: uniformly mixing a two-dimensional nanomaterial with a dispersant in a dispersion medium to form a stable dispersoid. The dispersant is selected from any one of the two-dimensional nanomaterial dispersants.

Furthermore, the two-dimensional nanomaterial is selected from a two-dimensional boron nitride nanomaterial and a two-dimensional molybdenum disulfide nanomaterial.

For example, the two-dimensional boron nitride nanomaterial or the two-dimensional molybdenum disulfide nanomaterial is selected from a nanosheet having a thickness of 1-20 nm.

Furthermore, a weight ratio of the dispersant to the two-dimensional nanomaterial is 0.1-10:1, and preferably 0.2-2:1.

Furthermore, the dispersion medium includes, but is not limited to, any one or a combination of two or more of water, an organic solvent, or a polymer resin.

A sixth aspect of an embodiment of the present disclosure further provides a redispersible two-dimensional nanomaterial powder, which is a powder obtained by removing the dispersion medium in any one of the two-dimensional nanomaterial dispersoids, and is capable of being directly redispersed in the dispersion medium.

A seventh aspect of an embodiment of the present disclosure further provides a two-dimensional nanomaterial dispersion and redispersion method implemented on the basis of a physical approach, including:

uniformly mixing a two-dimensional nanomaterial with a dispersant in a dispersion medium to form a stable dispersoid, the dispersant selected from any one of the two-dimensional nanomaterial dispersants;

removing the dispersion medium in the stable dispersoid to obtain a complex of the two-dimensional nanomaterial and the dispersant, and redispersing the complex in the dispersion medium to form the stable dispersoid again.

Furthermore, the two-dimensional nanomaterial is selected from a two-dimensional boron nitride nanomaterial and a two-dimensional molybdenum disulfide nanomaterial. Preferably, the two-dimensional boron nitride nanomaterial or the two-dimensional molybdenum disulfide nanomaterial is selected from a nanosheet having a thickness of 1-20 nm.

Furthermore, the dispersion medium includes any one or a combination of two or more of water, an organic solvent, or a polymer resin; and preferably, the dispersion medium includes water, and/or an organic solvent.

Furthermore, a weight ratio of the dispersant to the two-dimensional nanomaterial is 0.1-10:1, and preferably 0.2-2:1.

Furthermore, the boron nitride dispersion and redispersion method implemented on the basis of a physical approach includes: uniformly mixing a two-dimensional nanomaterial with a dispersant in water and/or an organic solvent to form a stable dispersion, and then drying the stable dispersion to form the complex in a powder form.

Furthermore, the drying approach is selected from, but is not limited to, at least one of spray drying, rotary evaporation, or vacuum drying.

Compared with the existing technologies, the present invention utilizes a readily synthesizable and inexpensive oligoaniline, oligoaniline derivative, polyaniline conducting polymer or the like as a dispersant of a two-dimensional nanomaterial (such as a two-dimensional boron nitride nanomaterial or a two-dimensional molybdenum disulfide nanomaterial), simply mixes the dispersant with boron nitride, molybdenum disulfide, or the like in a dispersion medium, such as water, an organic solvent, or a polymer resin, and can significantly improve dispersity and dispersion stability of the two-dimensional boron nitride nanomaterial or the molybdenum disulfide nanomaterial in the dispersion medium by a physical interaction therebetween; and can also obtain the two-dimensional nanomaterial, such as the boron nitride nanosheet or the molybdenum disulfide nanosheet, with the dispersant by a simple liquid phase exfoliation method, which is an environment friendly and efficient process with simple operations without impairing the physical structure and chemical properties of boron nitride, molybdenum disulfide, or the like, and facilitates large-scale implementation. In addition, the present invention is used in a dispersion medium for dispersion or exfoliation of the two-dimensional nanomaterial, especially can recycle water, the organic solvent, and the like, can reduce costs, and can reduce emissions of waste water, waste gas, and organic matters.

DETAILED DESCRIPTION OF EMBODIMENTS

Figure 1:
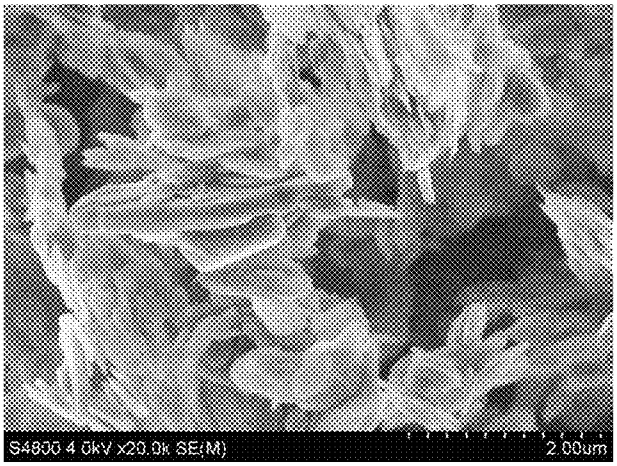
FIG. 1 is a SEM image of hexagonal boron nitride before exfoliation in example 1 of the present invention.

As mentioned above, in view of the defects of the existing technologies, the inventor of the present disclosure has presented the technical solutions of the present disclosure after prolonged and research and a lot of practice, and has obtained unexpectedly good technical effects. The technical solutions of the present disclosure and effects thereof will be illustrated in detail hereinafter.

Some embodiments of the present disclosure have provided a two-dimensional nanomaterial dispersant, including any one or a combination of two or more of an oligoaniline, an oligoaniline derivative, or a polyaniline conducting polymer, and capable of binding to a two-dimensional nanomaterial by a physical action to enable the two-dimensional nanomaterial to be stably dispersed in a dispersion medium.

Furthermore, the two-dimensional nanomaterial is selected from a two-dimensional boron nitride nanomaterial and a two-dimensional molybdenum disulfide nanomaterial.

Furthermore, stable dispersion of the two-dimensional boron nitride nanomaterial or two-dimensional molybdenum disulfide nanomaterial in the dispersion medium can be achieved only by simple physical mixing (e.g., a physically approach, such as mechanical stirring, ultrasound, or oscillation, which may also be, of course, supplemented with other appropriate non-physical approach in some embodiments), using weak interaction between the two-dimensional nanomaterial dispersant and boron nitride or molybdenum disulfide (especially a two-dimensional boron nitride nanomaterial or a two-dimensional molybdenum disulfide nanomaterial, e.g., a two-dimensional boron nitride nanosheet or a two-dimensional molybdenum disulfide nanosheet) without the addition of any additive and reactant.

Some embodiments of the present invention further provide a complex of a two-dimensional nanomaterial and the two-dimensional nanomaterial dispersant.

A weight ratio of the two-dimensional nanomaterial dispersant to the two-dimensional nanomaterial is preferably 0.1-10:1, and especially preferably 0.2-2:1.

Some embodiments of the present invention further provide use of an oligoaniline, an oligoaniline derivative, or a polyaniline conducting polymer as a boron nitride dispersant.

Some embodiments of the present invention further provide a preparation method of a two-dimensional nanomaterial by liquid phase exfoliation, including: fully mixing (e.g., by a physical approach, such as mechanical mixing, or ultrasound) the two-dimensional nanomaterial dispersant with boron nitride or molybdenum disulfide (particularly powder) in a dispersion medium (preferably water, a water solution, or an organic solvent), to form a stable dispersion of the two-dimensional nanomaterial.

Furthermore, the preparation method by liquid phase exfoliation further includes: centrifuging the stable dispersion of the two-dimensional nanomaterial to collect a complex of the two-dimensional nanomaterial and the two-dimensional nanomaterial dispersant.

Some embodiments of the present disclosure further provide a two-dimensional nanomaterial dispersoid, including: a dispersion medium; and a complex of any one of the two-dimensional nanomaterial and the two-dimensional nanomaterial dispersant dispersed in the dispersion medium.

Furthermore, the two-dimensional nanomaterial dispersoid is a fluid dispersoid, and preferably a liquid dispersoid or slurry.

Furthermore, in the complex of the two-dimensional nanomaterial and the two-dimensional nanomaterial dispersant, a weight ratio of the two-dimensional nanomaterial dispersant to the two-dimensional nanomaterial is 0.1-10:1.

Preferably, in the complex of the two-dimensional nanomaterial and the two-dimensional nanomaterial dispersant, the weight ratio of the two-dimensional nanomaterial dispersant to the two-dimensional nanomaterial is 0.2-2:1.

Furthermore, the two-dimensional nanomaterial dispersoid includes a two-dimensional nanomaterial of less than 10 mg/mL.

That is, it may be considered that, furthermore, by physically binding to the two-dimensional nanomaterial dispersant, the maximum dispersity of the two-dimensional nanomaterial in a dispersion medium (e.g., water or an organic solvent) can reach 10 mg/mL. It should be noted that the "maximum dispersity" here corresponds to use of a minimum effective amount of the two-dimensional nanomaterial dispersant.

Some embodiments of the present invention further provide a preparation method of a two-dimensional nanomaterial dispersoid, including: uniformly mixing a two-dimensional nanomaterial with a dispersant in a dispersion medium to form a stable dispersoid. The dispersant is selected from any one of the two-dimensional nanomaterial dispersants.

Furthermore, a weight ratio of the dispersant to the two-dimensional nanomaterial is 0.1-10:1, and preferably 0.2-2:1.

Some embodiments of the present disclosure further provide a redispersible two-dimensional nanomaterial powder, which is a powder obtained by removing the dispersion medium (preferably a volatile dispersion medium, such as water, or an organic solvent) in any one of the two-dimensional nanomaterial dispersoids, and is capable of being directly redispersed in the dispersion medium.

Some embodiments of the present disclosure further provide a two-dimensional nanomaterial dispersion and redispersion method implemented on the basis of a physical approach, including:

uniformly mixing a two-dimensional nanomaterial with a dispersant in a dispersion medium to form a stable dispersoid, the dispersant selected from any one of the two-dimensional nanomaterial dispersants;

removing the dispersion medium in the stable dispersoid to obtain a complex of the two-dimensional nanomaterial and the dispersant, and redispersing the complex in the dispersion medium to form the stable dispersoid again.

Furthermore, a weight ratio of the dispersant to the two-dimensional nanomaterial is 0.1-10:1, and preferably 0.2-2:1.

Furthermore, the boron nitride dispersion and redispersion method implemented on the basis of a physical approach includes: uniformly mixing a two-dimensional nanomaterial with a dispersant in water and/or an organic solvent to form a stable dispersion, and then drying the stable dispersion to form the complex in a powder form.

The drying approach at least may be selected from, but is not limited to, any one of spray drying, rotary evaporation, or vacuum drying.

The oligoaniline is also known as an aniline oligomer, an aniline conjugated chain segment contained therein is shorter than the polyaniline, its electroactivity is similar to that of the polyaniline, but it has no defects in its molecule, and has better solubility. The oligoaniline applicable to the present invention may be preferably selected from, but is not limited to, any one or a combination of more of an aniline trimer, an aniline tetramer, an aniline pentamer, or an aniline hexamer.

The oligoaniline derivative is mainly formed on the basis of the oligoaniline, and the interpretation of the oligoaniline is as described hereinbefore.

Preferably, the oligoaniline derivative may be selected from, but is not limited to, one derivative or a combination of a plurality of derivatives of any one of the aniline trimer, the aniline tetramer, the aniline pentamer, or the aniline hexamer.

Furthermore, the oligoaniline derivative includes a carboxylic acid end-capped oligoaniline derivative, an oligoaniline binding to a functional group, or a small molecular compound containing an oligoaniline. Preferably, the functional group includes, but is not limited to, any one or a combination of two or more of alkoxy, carboxyl, sulfo, or phosphoryl.

Preferably, the oligoaniline derivative is selected from an oligoaniline graft or block polymer.

Preferably, the oligoaniline derivative has any one of following chemical formulas:

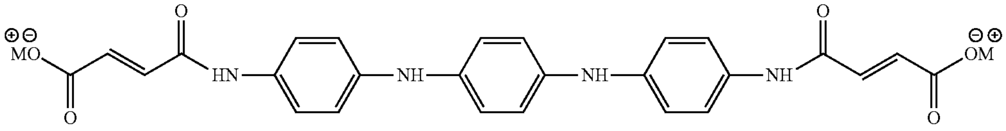

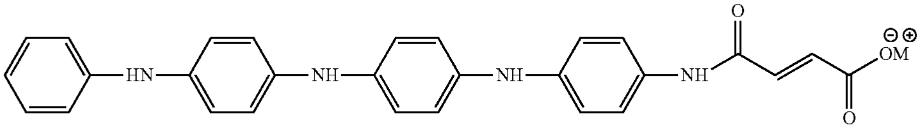

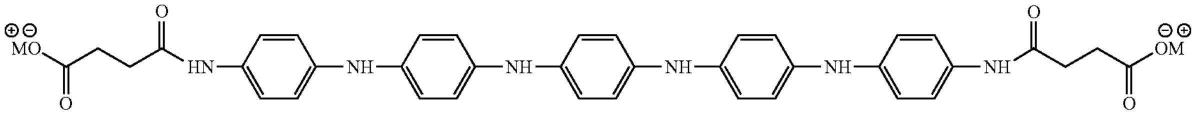

-continued

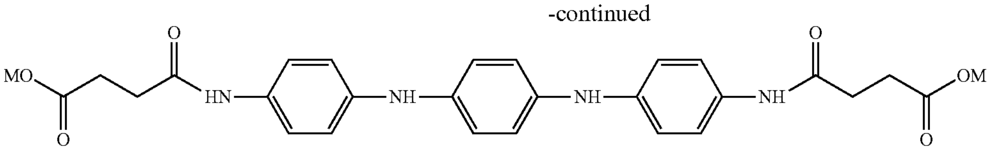

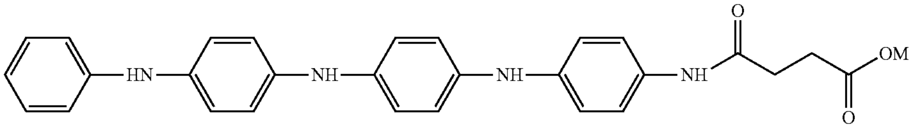

where M includes, but is not limited to, $Na^+$, $K^+$, potassium or quaternary ammonium salt cation.

The oligoanilines or oligoaniline derivatives may be obtained from commercially available approaches, or independently prepared by referring to references (e.g., *CHEM. COMMUN.,* 2003, pp. 2768-2769*; Synthetic Metals,* 2001, Vol. 122, pp. 237-242; CN101811997A; CN 1369478A, or CN 1204655A).

The polyaniline conducting polymer includes, but is not limited to, any one or a combination of two or more of an eigenstate polyaniline, a doped polyaniline, a substituted polyaniline, an oil soluble polyaniline, or a water soluble polyaniline.

Preferably, the polyaniline conducting polymer includes a polyaniline conducting polymer having a structural unit represented by any one of chemical formulas (1)-(3):

(1)

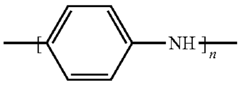

(2)

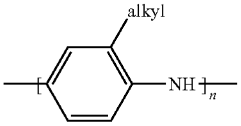

(3)

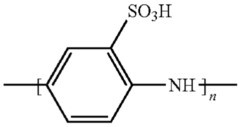

where, n=3-500.

The polyaniline conducting polymer applicable to the present invention can be obtained from commercially available approaches, or independently prepared by referring to references (e.g., *Journal of Polymer Science,* 2000, 38: 194-195, 203*; Materials Review,* 2001, 15 (3): 42*; Journal of Solid State Chemistry,* 2006, 179 (1): 308-314*; Chem. Commun.,* 1977, 16: 578-580).

The dispersion medium includes, but is not limited to, any one or a combination of two or more of water, an organic solvent, or a polymer resin.

For example, in some embodiments, the dispersion medium is selected from a low boiling solvent, and/or a high boiling polar organic solvent, e.g., may be selected from, but is not limited to, any one or a combination of two or more of ethanol, tetrahydrofuran, N,N-dimethylformamide, dimethyl sulfoxide, chloroform, or N-methylpyrrolidone.

For example, in some other embodiments, the dispersion medium may be selected from water and a water solution, e.g., an alkaline water solution containing an alkaline substance.

Alternatively, in some other embodiments, the dispersion medium may be selected from, but is not limited to, a polymer resin, e.g., polyethylene glycol, and polypropylene glycol.

Preferably, the two-dimensional boron nitride nanomaterial or the two-dimensional molybdenum disulfide nanomaterial is selected from a nanosheet having a thickness of 1-20 nm.

In some more specific embodiments, an oligoaniline is fully mixed with boron nitride in a dispersion medium with the oligoaniline as a two-dimensional nanomaterial dispersant by any one or more of physical approaches, such as ultrasound, stirring, or oscillation, to enable the oligoaniline to bind to boron nitride (especially a two-dimensional boron nitride nanomaterial) by a physical action, and then enable the maximum dispersity of boron nitride (especially a two-dimensional boron nitride nanomaterial) in the dispersion medium (especially the organic solvent) to reach 10 mg/mL (preferably 0.01 mg/mL-5 mg/mL, and especially preferably 0.1 mg/mL-5 mg/mL).

In some more specific embodiments, a two-dimensional boron nitride nanomaterial dispersoid may include: a dispersion medium (preferably the organic solvent); and a complex of the two-dimensional boron nitride nanomaterial and an oligoaniline dispersed in the dispersion medium.

In some more specific embodiments, a redispersible two-dimensional boron nitride nanomaterial powder may be a powder obtained by removing a dispersion medium (preferably the organic solvent) in any one of the boron nitride dispersoids, and can be directly redispersed in the dispersion medium. The dispersion medium can be recycled.

In some more specific embodiments, a two-dimensional boron nitride nanomaterial may be uniformly mixed with an oligoaniline in an organic solvent to form a stable dispersion, and then the stable dispersion is dried (i.e., removing the organic solvent) by any one of the drying approaches to form a complex of the two-dimensional boron nitride nanomaterial in a powder form and the oligoaniline.

In these specific embodiments, the dispersion medium is preferably an organic solvent, and is preferably selected from a low boiling solvent, and/or a high boiling polar organic solvent, e.g., may be preferably selected from, but is not limited to, any one or more of ethanol, tetrahydrofuran, N,N-dimethylformamide, dimethyl sulfoxide, chloroform, or N-methylpyrrolidone.

In these specific embodiments, exfoliation and good dispersion of the two-dimensional boron nitride nanomaterial in the dispersion medium (preferably an organic solvent) can be achieved with the help of a physical interaction between the oligoaniline and boron nitride. The whole exfoliation process involves simple operations without the need for harsh reaction conditions (e.g., reaction conditions, such as high temperature, high pressure, strong acid, or strong alkali), and facilitates large-scale production and development of use of downstream products thereof.

In some more specific embodiments, an oligoaniline derivative is fully mixed with boron nitride in a dispersion medium with the oligoaniline derivative as a two-dimensional nanomaterial dispersant by any one or more of physical approaches, such as ultrasound, stirring, or oscillation, to enable the oligoaniline to bind to boron nitride (especially a two-dimensional boron nitride nanomaterial) by a physical action, then enable the maximum dispersity of boron nitride (especially a two-dimensional boron nitride nanomaterial) in the dispersion medium (e.g., water, especially an alkaline water solution) to reach 10 mg/mL (preferably less than 5 mg/mL), and especially preferably enable the oligoaniline to stably exist for a long time at a dispersity of 0.1 mg/mL-5 mg/mL).

any one of the drying approaches to form a complex of the two-dimensional boron nitride nanomaterial in a powder form and the oligoaniline derivative.

The dispersion medium may be selected from the group consisting of water, the organic solvent, the polymer resin, and the like, but is preferably selected from water and a water solution, and is especially preferably an alkaline water solution.

The alkali includes, but is not limited to, NaOH, KOH, or ammonia water.

In these specific embodiments, the oligoaniline derivative may be preferably selected from a carboxylic acid end-capped oligoaniline derivative, and an oligoaniline binding to a functional group (e.g., alkoxy, carboxyl, sulfo, or phosphoryl). For example, the oligoaniline derivative has any one of following chemical formulas:

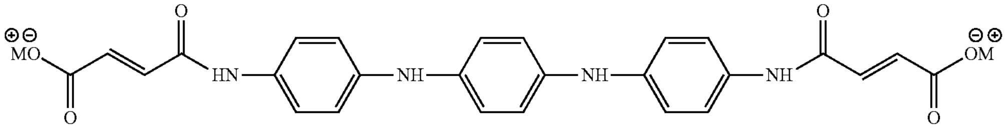

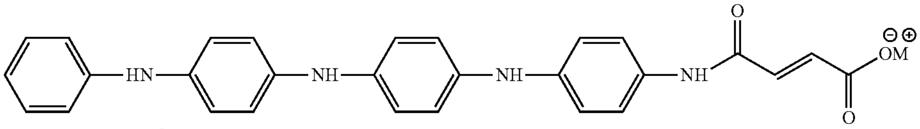

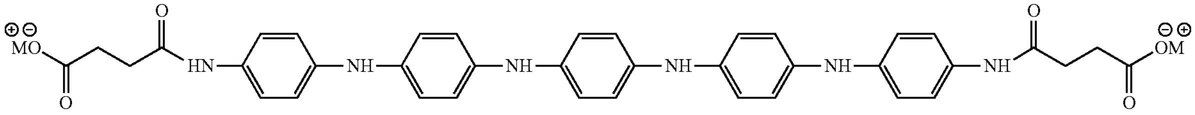

In some more specific embodiments, a preparation method of a two-dimensional boron nitride nanomaterial by liquid phase exfoliation may include: fully mixing an oligoaniline derivative, an alkali that is optionally added or not with a boron nitride powder in a dispersion medium to form a stable dispersion of the two-dimensional boron nitride nanomaterial by at least one of physical approaches, such as ultrasound, stirring, or oscillation.

Furthermore, the oligoaniline derivative and an alkali can be fully mixed with a boron nitride powder in water to form a stable dispersion of a two-dimensional boron nitride nanomaterial, and then the stable dispersion can be centrifuged to collect a complex of the two-dimensional boron nitride nanomaterial and the oligoaniline derivative.

In some more specific embodiments, a two-dimensional boron nitride nanomaterial dispersoid may include: a dispersion medium (preferably a water phase system, such as water or a water solution, and especially preferably an alkaline water solution); and a complex of the two-dimensional boron nitride nanomaterial and an oligoaniline derivative dispersed in the dispersion medium.

In some more specific embodiments, a redispersible two-dimensional boron nitride nanomaterial powder may be a powder obtained by removing a dispersion medium (preferably water or a water solution) in any one of the boron nitride dispersoids, and can be directly redispersed in the dispersion medium. The dispersion medium can be recycled.

In some more specific embodiments, a two-dimensional boron nitride nanomaterial can be uniformly mixed with an oligoaniline derivative in water or an alkaline water solution to form a stable dispersion, and then the stable dispersion is dried (i.e., removing water or the alkaline water solution) by where M includes $Na^+$, $K^+$, potassium or quaternary ammonium salt cation.

In the specific embodiments, exfoliation and good dispersion of the two-dimensional boron nitride nanomaterial in the dispersion medium (preferably water or a water solution, and especially preferably an alkaline water solution) can be achieved with the help of a physical interaction between the oligoaniline derivative and the two-dimensional boron nitride nanomaterial. The whole exfoliation process involves simple operations without the need for harsh reaction conditions (e.g., reaction conditions, such as high temperature, high pressure, strong acid, or strong alkali), and facilitates large-scale production and development of use of downstream products thereof.

In some more specific embodiments, a polyaniline conducting polymer can be fully mixed with boron nitride in a dispersion medium with the polyaniline conducting polymer as a two-dimensional nanomaterial dispersant by any one or more of physical approaches, such as ultrasound, stirring, or oscillation, to enable the polyaniline conducting polymer to bind to boron nitride (especially a two-dimensional boron nitride nanomaterial) by a physical action, then enable the maximum dispersity of boron nitride (especially a two-dimensional boron nitride nanomaterial) in the dispersion medium (e.g., water and/or the organic solvent) to reach 10 mg/mL (preferably less than 5 mg/mL), and especially preferably enable the polyaniline conducting polymer to stably exist for a long time at a dispersity of 0.1 mg/mL-5 mg/mL).

In some more specific embodiments, a preparation method of a two-dimensional boron nitride nanomaterial by liquid phase exfoliation may include: fully mixing a polyaniline conducting polymer, with a boron nitride powder in a dispersion medium to form a stable dispersion of the two-dimensional boron nitride nanomaterial by at least one of physical approaches, such as ultrasound, stirring, or oscillation.

Furthermore, the stable dispersion can be centrifuged to collect a complex of the two-dimensional boron nitride nanomaterial and the polyaniline conducting polymer.

In some more specific embodiments, a two-dimensional boron nitride nanomaterial dispersoid may include: a dispersion medium (preferably water and/or the organic solvent); and a complex of the two-dimensional boron nitride nanomaterial and a polyaniline conducting polymer dispersed in the dispersion medium. The two-dimensional boron nitride nanomaterial dispersoid here is preferably a liquid dispersoid, slurry, or the like.

In some more specific embodiments, a redispersible two-dimensional boron nitride nanomaterial powder may be a powder obtained by removing a dispersion medium (e.g., water and/or the organic solvent) in any one of the boron nitride dispersoids, and can be directly redispersed in the dispersion medium. The dispersion medium can be recycled.

In some more specific embodiments, a two-dimensional boron nitride nanomaterial may be uniformly mixed with a polyaniline conducting polymer in water and/or the organic solvent to form a stable dispersion, and then the stable dispersion is dried (i.e., removing water and/or the organic solvent) by any one of the drying approaches to form a complex of the two-dimensional boron nitride nanomaterial in a powder form and the polyaniline conducting polymer.

The dispersion medium includes any one or a combination of two or more of water, the organic solvent, or the polymer resin, and is preferably selected from an organic solvent, e.g., a plurality of the organic solvents enumerated hereinbefore.

The method for liquid phase exfoliation of boron nitride according to the present invention can achieve exfoliation and good dispersion of a two-dimensional boron nitride nanomaterial in a dispersion medium, such as water and/or an organic solvent, with the help of a physical interaction between a polyaniline conducting polymer and the two-dimensional boron nitride nanomaterial. The whole exfoliation process involves simple operations without the need for harsh reaction conditions (e.g., reaction conditions, such as high temperature, high pressure, strong acid, or strong alkali), and facilitates large-scale production and development of use of downstream products thereof.

With the embodiments, preparation, dispersion, and redispersion of a two-dimensional boron nitride nanomaterial by liquid phase exfoliation can be achieved simply and inexpensively on a large scale. In particular, the obtained redispersible boron nitride composite powder (mainly including a complex of the two-dimensional boron nitride nanomaterial and the two-dimensional nanomaterial dispersant) has broad application prospects in the fields, such as functional coatings, thermal conduction, and composite material enhancement.

In some more specific embodiments, an oligoaniline or derivative thereof is fully mixed with molybdenum disulfide in a dispersion medium (e.g., water, a water solution, and/or the organic solvent) with the oligoaniline or derivative thereof as a two-dimensional nanomaterial dispersant by any one or more of physical approaches, such as ultrasound, stirring, or oscillation, to enable the oligoaniline or derivative thereof to bind to molybdenum disulfide (especially a two-dimensional molybdenum disulfide nanomaterial) by a physical action, and then enable the maximum dispersity of molybdenum disulfide (especially a two-dimensional molybdenum disulfide nanomaterial) in the dispersion medium (e.g., water, a water solution, and/or the organic solvent) to reach 10 mg/mL (preferably 0.1 mg/mL-10 mg/mL, and especially preferably 0.1 mg/mL-2.5 mg/mL).

In some more specific embodiments, a two-dimensional molybdenum disulfide nanomaterial dispersoid may include: a dispersion medium (e.g., water, a water solution, and/or the organic solvent); and a complex of the two-dimensional molybdenum disulfide nanomaterial and an oligoaniline or derivative thereof dispersed in the dispersion medium.

In some more specific embodiments, a redispersible two-dimensional molybdenum disulfide nanomaterial powder may be a powder obtained by removing a dispersion medium (e.g., water, a water solution, and/or the organic solvent) in any one of the molybdenum disulfide nanomaterial dispersoids, and can be directly redispersed in the dispersion medium. The dispersion medium can be recycled.

In some more specific embodiments, an oligoaniline and/or an oligoaniline derivative and an alkali (e.g., NaOH, or KOH) can be fully mixed with a molybdenum disulfide powder in water to form a stable dispersion of a two-dimensional molybdenum disulfide nanomaterial, and then the stable dispersion can be centrifuged to collect a complex of the two-dimensional molybdenum disulfide nanomaterial and the oligoaniline and/or the oligoaniline derivative.

In these specific embodiments, the dispersion medium may be selected from the group consisting of water, the organic solvent, the polymer resin, and the like, but is preferably selected from water and a water solution, and is especially preferably an alkaline water solution.

In these specific embodiments, the oligoaniline derivative includes a small molecule compound containing an oligoaniline, and is especially a carboxyl end-capped oligoaniline derivative, an alkyl-substituted oligoaniline derivative, or the like, e.g., carboxyl end-capped aniline trimer, tetramer or pentamer, or long-chain alkyl or alkoxy end-capped aniline trimer, tetramer or pentamer. Preferably, the oligoaniline derivative may be selected from an oligoaniline graft or block polymer, e.g., a polyethylene glycol end-capped oligoaniline (polyethylene glycol end-capped aniline trimer, tetramer, pentamer, or the like); a polylactic acid end-capped oligoaniline (polylactic acid end-capped aniline trimer, tetramer, pentamer, or the like). More specifically, the oligoaniline derivative may be preferably selected from a compound having any one of following chemical formulas:

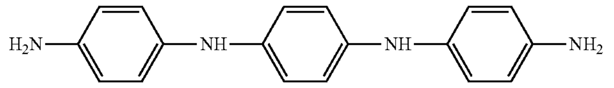

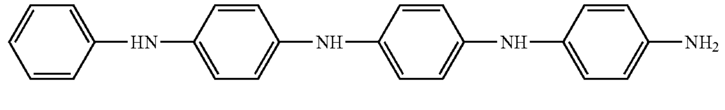

-continued

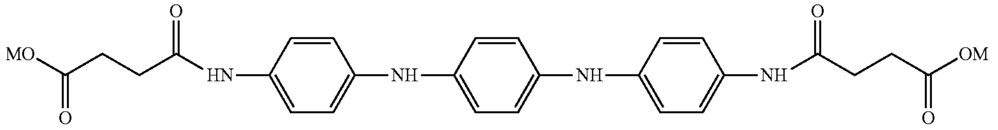

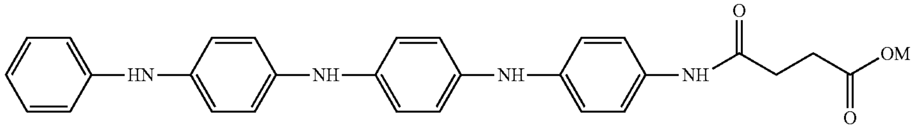

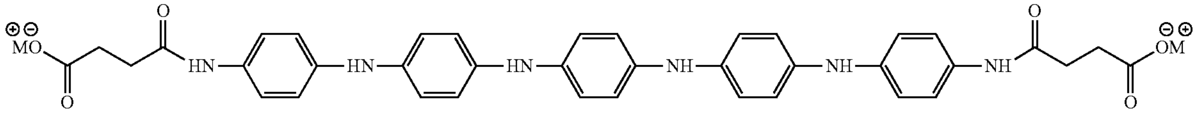

where M includes $H^+$, $Na^+$, $K^+$ or a quaternary ammonium salt cation.

In these specific embodiments, exfoliation and good dispersion of the two-dimensional molybdenum disulfide nanomaterial in the dispersion medium, such as water and/or an organic solvent, can be achieved with the help of a physical interaction between the oligoaniline and/or the oligoaniline derivative and the two-dimensional molybdenum disulfide nanomaterial. The whole exfoliation process is environment friendly and efficient with simple operations without the need for harsh reaction conditions (e.g., reaction conditions, such as high temperature, high pressure, strong acid, or strong alkali), and facilitates large-scale production and development of use of downstream products thereof.

In some more specific embodiments, a polyaniline conducting polymer can be fully mixed with molybdenum disulfide in a dispersion medium with the polyaniline conducting polymer as a two-dimensional nanomaterial dispersant by any one or more of physical approaches, such as ultrasound, stirring, or oscillation, to enable the polyaniline conducting polymer to bind to molybdenum disulfide (especially a two-dimensional molybdenum disulfide nanomaterial) by a physical action, then enable the maximum dispersity of molybdenum disulfide (especially a two-dimensional molybdenum disulfide nanomaterial) in the dispersion medium (e.g., water, and/or the organic solvent) to reach 5 mg/mL, and especially preferably enable the polyaniline conducting polymer to stably exist for a long time at a dispersity of 0.1 mg/mL-3 mg/mL).

In some more specific embodiments, a preparation method of a two-dimensional molybdenum disulfide nanomaterial by liquid phase exfoliation may include: fully mixing a polyaniline conducting polymer with a molybdenum disulfide powder in a dispersion medium to form a stable dispersion of the two-dimensional molybdenum disulfide nanomaterial by at least one of physical approaches, such as ultrasound, stirring, or oscillation.

Furthermore, the stable dispersion can be centrifuged to collect a complex of the two-dimensional molybdenum disulfide nanomaterial and the polyaniline conducting polymer.

In some more specific embodiments, a two-dimensional molybdenum disulfide nanomaterial dispersoid may include: a dispersion medium (e.g., water, and/or the organic solvent); and a complex of the two-dimensional molybdenum disulfide nanomaterial and a polyaniline conducting polymer dispersed in the dispersion medium. The two-dimensional molybdenum disulfide nanomaterial dispersoid here is preferably a liquid dispersoid, slurry, or the like.

In some more specific embodiments, a redispersible two-dimensional molybdenum disulfide nanomaterial powder may be a powder obtained by removing a dispersion medium (e.g., water, and/or the organic solvent) in any one of the molybdenum disulfide nanomaterial dispersoids, and can be directly redispersed in the dispersion medium. The dispersion medium can be recycled.

In some more specific embodiments, a two-dimensional molybdenum disulfide nanomaterial may be uniformly mixed with a polyaniline conducting polymer in water and/or the organic solvent to form a stable dispersion, and then the stable dispersion is dried (i.e., removing water and/or the organic solvent) by any one of the drying approaches to form a complex of the two-dimensional molybdenum disulfide nanomaterial in a powder form and the polyaniline conducting polymer.

The dispersion medium includes any one or a combination of two or more of water, the organic solvent, or the polymer resin, and is preferably selected from water and an organic solvent, e.g., a plurality of the organic solvents enumerated hereinbefore.

The method for liquid phase exfoliation of boron nitride according to the present invention can achieve exfoliation and good dispersion of a two-dimensional molybdenum disulfide nanomaterial in a dispersion medium, such as water and/or an organic solvent, with the help of a physical interaction between a polyaniline conducting polymer and the two-dimensional molybdenum disulfide nanomaterial. The whole exfoliation process involves simple operations without the need for harsh reaction conditions (e.g., reaction conditions, such as high temperature, high pressure, strong acid, or strong alkali), and facilitates large-scale production and development of use of downstream products thereof.

With the embodiments, preparation, dispersion, and redispersion of a two-dimensional molybdenum disulfide nanomaterial by liquid phase exfoliation can be achieved simply and inexpensively on a large scale. In particular, the obtained redispersible molybdenum disulfide composite powder (mainly including a complex of the two-dimensional molybdenum disulfide nanomaterial and the two-dimensional nanomaterial dispersant) has broad application prospects in the fields, such as functional coatings, thermal conduction, and composite material enhancement. In particular, the exfoliated two-dimensional molybdenum disulfide nanosheet is expected to have broad application prospects in the fields, such as semiconductors, energy, wear resistant lubricating coatings, or composite materials.

The technical solutions in embodiments of the present disclosure will be illustrated in detail hereinafter in conjunction with some embodiments and the accompanying drawings. Obviously, only a part of the embodiments, instead of all embodiments, of the present disclosure are presented. All other embodiments concluded by those skilled in the art based on the embodiments of the present disclosure without making inventive labor fall within the scope of protection of the present disclosure.

Example 1: Synthesis of Aniline Trimer and Use Thereof in the Exfoliation of a Two-Dimensional Boron Nitride Nanosheet in an Organic Solvent Synthesis of aniline trimer: p-phenylenediamine sulfate (8.87 g), and aniline (5.56 g) were added to a hydrochloric acid solution (1M, 500 mL) present in a three-necked flask, and cooled to −5° C. A hydrochloric acid (1M, 150 mL) solution of ammonium persulfate (13.62 g) was slowly dropwise added to the reaction flask through a dropping funnel. On completion of the dropwise addition, the resulting solution was further stirred for additional 1 h. The reaction product was filtered under suction, and washed with a considerable amount of deionized water, to obtain a dark green solid product. Then the product was washed with 10% aqueous ammonia solution, then washed with deionized water twice, and finally dried and kept in a vacuum oven at 40° C. for later use.

The obtained aniline trimer and boron nitride powder were mixed at a certain ratio, dissolved in ethanol (EtOH) and tetrahydrofuran (THF) respectively, and ultrasonically dispersed for 10 min, to test the dispersion effect of boron nitride in the presence of an oligoaniline, as shown in Table 1 and Table 2.

Figure 2:
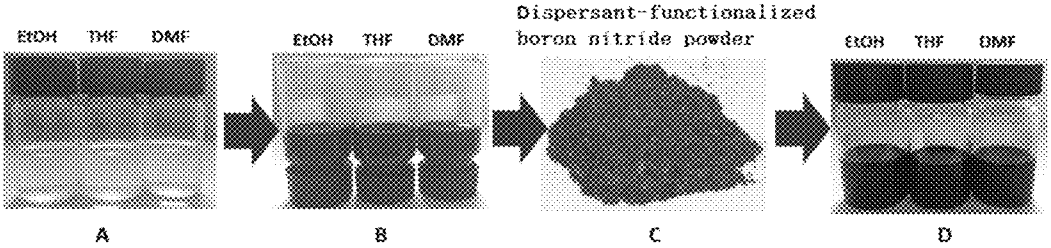
FIG. 2 is photos of dispersion and redispersion of boron nitride in the absence of a dispersant and in the presence of a dispersant in example 1 of the present invention.

By referring to FIG. 2A, a boron nitride powder without addition of aniline trimer tended to aggregate in a conventional organic solvent, such as tetrahydrofuran (THF), or ethanol (EtOH). By further referring to FIG. 2B, boron nitride was exfoliated in the presence of an oligoaniline, and an aniline trimer-boron nitride complex can form a stable dispersion (boron nitride content can reach 5 mg/mL) in an organic solvent, such as ethanol, or tetrahydrofuran, without obvious precipitation. Please further refer to a dispersant-functionalized boron nitride powder (a two-dimensional boron nitride nanosheet), as shown in FIG. 2C. FIG. 2D shows that the dispersant-functionalized boron nitride powder can be stably redispersed in an organic solvent in the presence of an oligoaniline dispersant, and no obvious precipitation occurred within 30 d.

Figure 3A:
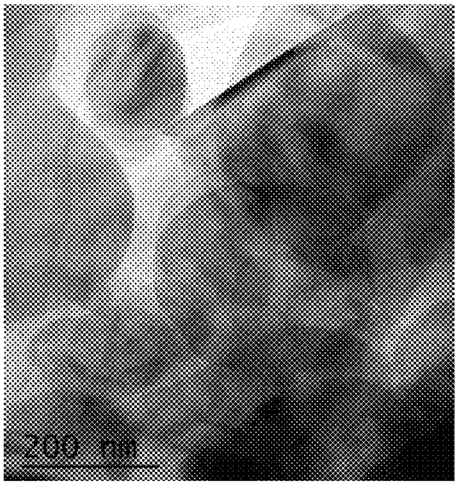
FIG. 3*a*-FIG. 3*b* are TEM images of an exfoliated two-dimensional boron nitride nanosheet in example 1 of the present invention.
Figure 3B:
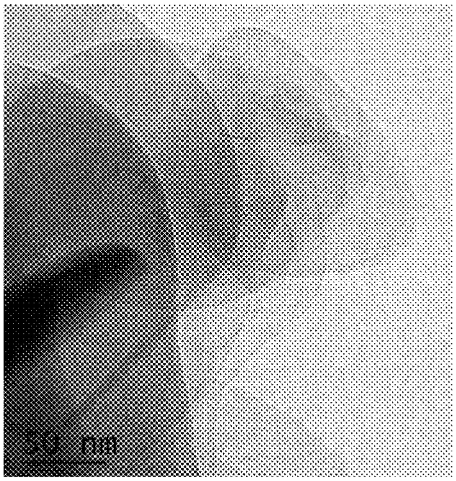

Furthermore, please refer to FIG. 3*a*-FIG. 3*b*, which show TEM images of an exfoliated typical two-dimensional boron nitride nanosheet (hexagonal boron nitride nanosheet) obtained in the example.

TABLE 1

Dispersibility of a Two-Dimensional Boron Nitride Nanosheet in Ethanol (mass ratio of aniline trimer to boron nitride = 1:2)

| 5 mg/10 mL | 10 mg/10 mL | 25 mg/10 mL | 50 mg/10 mL | 100 mg/10 mL |
|---|---|---|---|---|
| Good without obvious precipitation | Good without obvious precipitation | Good without obvious precipitation | Good without obvious precipitation | With a precipitate |

TABLE 2

Dispersibility of a Two-Dimensional Boron Nitride Nanosheet in THF (mass ratio of aniline trimer to boron nitride = 1:2)

| 5 mg/10 mL | 10 mg/10 mL | 25 mg/10 mL | 50 mg/10 mL | 100 mg/10 mL |
|---|---|---|---|---|
| Good | Good | Good | Good | With precipitation |

Example 2: Synthesis of Aniline Tetramer and Use Thereof in an Oil-Based Dispersion of Boron Nitride N-phenyl-p-phenylenediamine (11.08 g, 60 mmol), acetone (300 mL), a hydrochloric acid (1M, 75 mL) solution, and deionized water (300 mL) were successively added a 500 mL round bottom flask, and stirred until fully dissolved. Then a hydrochloric acid solution (1M, 150 mL) of ammonium persulfate (13.6 g, 60 mmol) was gradually added dropwise to the solution. On completion of the dropwise addition, the resulting solution was kept at −5° C. for 3 h. On completion of the reaction, the resulting solution was filtered under suction by a Buchner funnel, then washed with 10 wt % ammonia water, then washed with a considerable amount of deionized water twice, and finally dried and kept in a vacuum oven at 40° C. for later use.

The obtained aniline tetramer and a boron nitride powder were dissolved in THF or DMF at a certain ratio, and ultrasonically dispersed for 10 min, to test its dispersion effect in the solvent, as shown in Table 3 and Table 4. When the concentration of the aniline tetramer-boron nitride complex was less than 5 mg/mL, a stable dispersion can be formed in tetrahydrofuran, and no obvious precipitation occurred within 30 d.

TABLE 3

Dispersion Effect of Aniline Tetramer-Boron Nitride in THF (weight ratio in this experiment was 1:2)

| 5 mg/10 mL | 10 mg/10 mL | 25 mg/10 mL | 50 mg/10 mL | 100 mg/10 mL |
|---|---|---|---|---|
| Good without obvious precipitation | Good without obvious precipitation | Good without obvious precipitation | Good without obvious precipitation | With a precipitate |

TABLE 4

Dispersion Effect of Aniline Tetramer-Boron Nitride in DMF (weight ratio in this experiment was 1:2)

| 5 mg/10 mL | 10 mg/10 mL | 25 mg/10 mL | 50 mg/10 mL | 100 mg/10 mL |
|---|---|---|---|---|
| Good without obvious precipitation | Good without obvious precipitation | Good without obvious precipitation | Good without obvious precipitation | With a precipitate |

Example 3: Synthesis of Carboxylic Acid End-Capped Aniline Trimer and Use Thereof in the Preparation of a Water-Based Dispersion of a Boron Nitride Nanosheet Aniline trimer used in this example was synthesized according to the reference (*Chem. Eur.* 1, 2008, 14, 2909).

The process includes: dissolving the aniline trimer (2.92 g) in 50 mL of THF, then adding maleic anhydride (2.46 g), keeping the resulting solution at 40° C. for 3 h, and precipitating the reaction product with petroleum ether, to obtain carboxyl end-capped aniline trimer (4.81 g).

Figure 4:
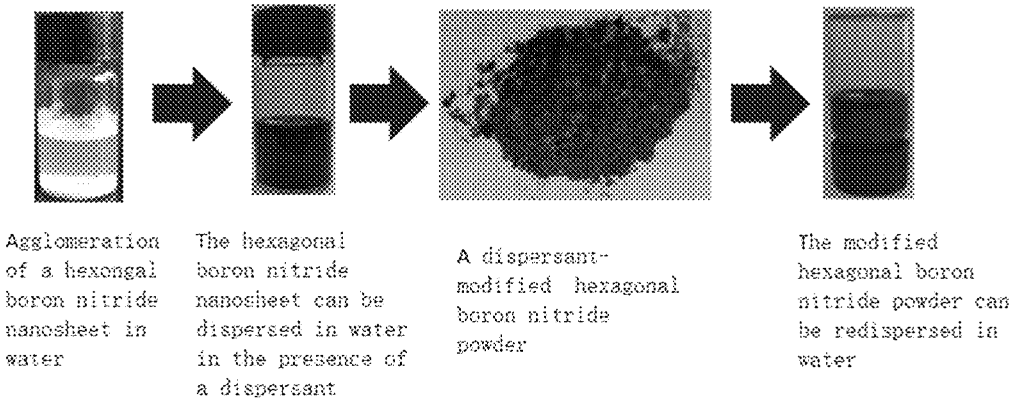
FIG. 4 is photos of dispersion and redispersion of boron nitride in the absence of a dispersant and in the presence of a dispersant in example 3 of the present invention.
Figure 5:
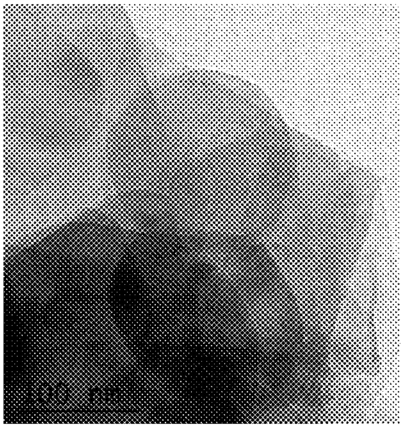
FIG. 5 is a TEM image of an exfoliated two-dimensional boron nitride nanosheet in example 3 of the present invention.

Water solutions of carboxylated aniline trimer, 2 molar equivalents of NaOH, and a hexagonal boron nitride powder (weight ratio of the hexagonal boron nitride powder to the carboxylated aniline trimer was 1:1) at different concentrations were prepared, and ultrasonically dispersed for 10 min. The dispersion effect was as shown in FIG. 4 and Table 5. When the concentration of the boron nitride nanosheet was less than 3 mg/mL, a stable dispersion can be formed, and no obvious precipitation occurred after it was kept at room temperature for 30 d (see FIG. 5 for the appearance), while when the concentration was 5 mg/mL, the boron nitride nanosheet tended to be saturated in water, and partial precipitation occurred after it was kept at room temperature for 1 d.

TABLE 5

Dispersion Effects of a Boron Nitride Nanosheet in Water at Different Concentrations in the Presence of Carboxyated Aniline Trimer

| 5 mg/10 mL | 15 mg/10 mL | 30 mg/10 mL | 50 mg/10 mL |
|---|---|---|---|
| Good without obvious precipitation | Good without obvious precipitation | Good without obvious precipitation | Good with partial precipitation |

Example 4: Synthesis of Carboxylic Acid End-Capped Aniline Tetramer and Use Thereof in the Preparation of a Water-Based Dispersion of a Boron Nitride Nanosheet Aniline tetramer used in this example was synthesized according to the reference (*Acta Chimica Sinica,* 2001, 69, 41). The process includes: adding the aniline tetramer (2.1 g) in 50 mL of THF, then adding maleic anhydride (0.68 g), and keeping the resulting solution at 40° C. for 3 h, to obtain a carboxyl derivative of aniline tetramer by precipitation with petroleum ether.

A water solution of the obtained carboxyl derivative of aniline tetramer, 2 molar equivalents of NaOH, and a hexagonal boron nitride powder at a certain concentration was prepared, and ultrasonically processed for 10 min. The dispersion effect was as shown in Table 6. When the concentration of the boron nitride nanosheet was less than 2.5 mg/mL, a uniform dispersion can be formed, while when the concentration was 5 mg/mL, the boron nitride nanosheet tended to be saturated in water, and partial precipitation occurred.

TABLE 6

Dispersion Effects of a Boron Nitride Nanosheet in Water at Different Concentrations in the Presence of Carboxyated Aniline Tetramer

| 5 mg/10 mL | 15 mg/10 mL | 30 mg/10 mL | 50 mg/10 mL |
|---|---|---|---|
| Good without obvious precipitation | Good without obvious precipitation | Good without obvious precipitation | Good with partial precipitation |

Example 5: Synthesis of Carboxylic Acid End-Capped Aniline Pentamer and Use Thereof in the Preparation of a Water-Based Dispersion of a Boron Nitride Nanosheet Carboxyl end-capped aniline pentamer used in this example was synthesized according to the reference (*Chemical Journal of Chinese Universities,* 2004, 9, 1768). The process includes: preparing a water solution of the obtained carboxyl derivative of aniline pentamer, 2 molar equivalents of NaOH, and boron nitride at a certain concentration, and ultrasonically processing the resulting solution for 10 min. The dispersion effect was as shown in Table 7. When the concentration of the boron nitride nanosheet was less than 2.5 mg/mL, a stable dispersion can be formed, while when the concentration was 5 mg/mL, the boron nitride nanosheet tended to be saturated in water, and partial precipitation occurred.

TABLE 7

Dispersion Effects of a Boron Nitride Nanosheet in Water at Different Concentrations in the Presence of Carboxyated Aniline Tetramer

| 5 mg/10 mL | 15 mg/10 mL | 30 mg/10 mL | 50 mg/10 mL |
|---|---|---|---|
| Good without obvious precipitation | Good without obvious precipitation | Good without obvious precipitation | Good with partial precipitation |

The stable boron nitride nanosheet dispersions obtained in Example 3-Example 5 were dried under vacuum to form boron nitride powders. When these powders were redispersed in water, stable dispersion systems can be formed by fierce stirring or ultrasound, and substantially no precipitation phenomena occurred after the dispersion systems were left to stand at room temperature for 30 d or more.

Example 6: Synthesis of an Eigenstate Polyaniline and Use Thereof in the Exfoliation of a Two-Dimensional Boron Nitride Nanosheet in an Organic Solvent Aniline (7 g) was dissolved in 100 mL of 1 M hydrochloric acid present in a 200 mL round bottom flask while stirring, and cooled to zero ° C. Then, 17 g of ammonium persulfate was dissolved in 50 mL of a 1M hydrochloric acid solution, and the resulting solution was slowly dropwise added to the round bottom flask. On completion of the dropwise addition, the resulting solution was kept for 12 h, and the reaction solution was filtered, and washed with distilled water twice to obtain a dark green doped polyaniline. The obtained dark green polyaniline was immersed in 10% ammonia water for 12 h, filtered, washed with distilled water until the filtrate was neutral, and dried under vacuum at 65° C. for 24 h, to obtain an eigenstate polyaniline (5.2 g) for later use. The eigenstate polyaniline has good solubility in a strongly polar solvent, such as DMF, or NMP.

Figure 6A:
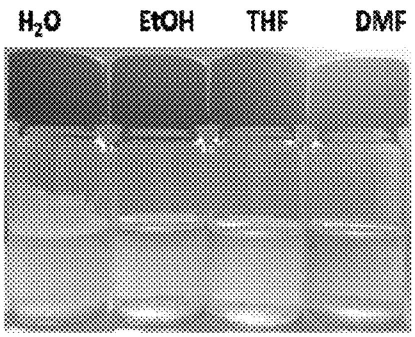
FIG. 6*a*-FIG. 6*b* are photos of dispersion and redispersion of boron nitride in the absence of a dispersant and in the presence of a dispersant in example 6 of the present invention.
Figure 6B:
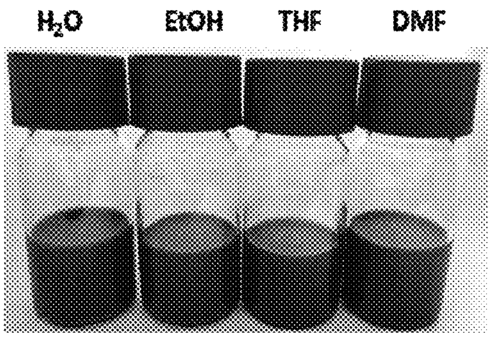
Figure 7:
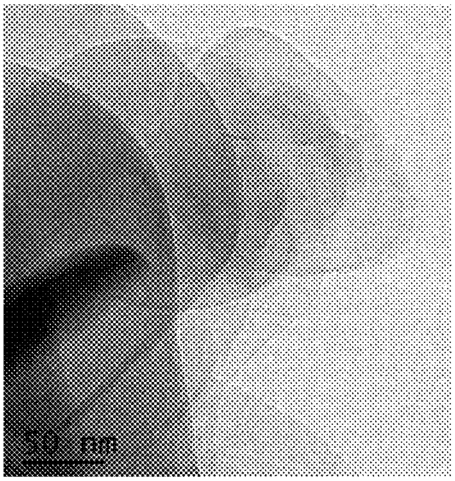
FIG. 7 is a TEM image of an exfoliated two-dimensional boron nitride nanosheet in example 6 of the present invention.

The eigenstate polyaniline prepared in this example, a boron nitride powder, and DMF were mixed at a certain ratio, and ultrasonically dispersed for 10 min, to test the dispersion effect of boron nitride in the presence of the polyaniline. The boron nitride nanosheet was exfoliated in the presence of the polyaniline (see FIG. 7 for the appearance after exfoliation). When the concentration of the boron nitride nanosheet was less than 5 mg/mL, a stable dispersion can be formed, and no obvious precipitation occurred after it was left to stand for 30 d, while when the concentration of the boron nitride nanosheet reached 10 mg/mL, a certain degree of precipitation would occur (see FIG. 6*a* and Table 8).

TABLE 8

Dispersibility of a Two-Dimensional Boron Nitride Nanosheet in DMF (mass ratio of polyaniline to boron nitride = 1:1)

| 5 mg/10 mL | 10 mg/10 mL | 30 mg/10 mL | 50 mg/10 mL | 100 mg/10 mL |
|---|---|---|---|---|
| Good without obvious precipitation | Good without obvious precipitation | Good without obvious precipitation | Good without obvious precipitation | With a precipitate |

Example 7: Synthesis of an Alkyl-Substituted Polyaniline and Use Thereof in the Exfoliation of a Two-Dimensional Boron Nitride Nanosheet in an Organic Solvent isopropylaniline (6.0 g) was dissolved in 100 mL of 1 M hydrochloric acid present in a 200 mL round bottom flask while stirring, and cooled to zero ° C. Then, 11.44 g of ammonium persulfate was dissolved in 50 mL of a 1M hydrochloric acid solution, and the resulting solution was slowly dropwise added to the round bottom flask. On completion of the dropwise addition, the resulting solution was kept for 12 h, and the reaction solution was filtered, and washed with distilled water twice to obtain a dark green doped isopropyl polyaniline. The obtained dark green polyaniline was immersed in 10% ammonia water for 12 h, filtered, washed with distilled water until the filtrate was neutral, and dried under vacuum at 65° C. for 24 h, to obtain an eigenstate isopropyl-substituted polyaniline (4.6 g) for later use. The eigenstate isopropyl polyaniline has good solubility in a polar solvent, such as THF, $CHCl_3$, DMF, or NMP.

The eigenstate isopropyl polyaniline prepared in this example, a boron nitride powder, and THF were mixed at a certain ratio, and ultrasonically dispersed for 10 min, to test the dispersion effect of boron nitride in the presence of the isopropyl-substituted polyaniline. The boron nitride nanosheet was exfoliated in the presence of the isopropyl-substituted polyaniline. When the concentration of the boron nitride nanosheet was less than 5 mg/mL, a stable dispersion was formed, while when the concentration of the boron nitride nanosheet reached 10 mg/mL, a certain degree of precipitation would occur due to very high concentration of the nanosheet (see Table 9).

TABLE 9

Dispersibility of a Two-Dimensional Boron Nitride Nanosheet in DMF (mass ratio of polyaniline to boron nitride = 1:1)

| 5 mg/10 mL | 10 mg/10 mL | 30 mg/10 mL | 50 mg/10 mL | 100 mg/10 mL |
|---|---|---|---|---|
| Good without obvious precipitation | Good without obvious precipitation | Good without obvious precipitation | Good without obvious precipitation | With a precipitate |

Example 8: Synthesis of a Sulfo-Substituted Polyaniline and Use Thereof in the Exfoliation of a Two-Dimensional Boron Nitride Nanosheet anilinesulfonic acid (4.3 g) and aniline (2.3 g) were dissolved in 250 mL of 1 M hydrochloric acid present in a 200 mL round bottom flask while stirring, and cooled to zero ° C. Then, 11.39 g of ammonium persulfate was dissolved in 150 mL of a 1M hydrochloric acid solution, and the resulting solution was slowly dropwise added to the round bottom flask. On completion of the dropwise addition, the resulting solution was kept for 12 h, the reaction solution was centrifuged, and the precipitate was washed with distilled water twice to obtain a dark green sulfonated aniline copolymer for later use. The sulfonated aniline copolymer has good solubility in a solvent, such as $H_2O$, EtOH, THF, DMF, or NMP.

The sulfonated aniline copolymer prepared in this example, a boron nitride powder, and water (or ethanol) were mixed at a certain ratio, and ultrasonically dispersed for 10 min, to test the dispersion effect of a boron nitride nanosheet. The boron nitride nanosheet was exfoliated in the presence of the sulfonated polyaniline. When the concentration of the boron nitride nanosheet was less than 5 mg/mL, a stable dispersion can be formed, while when the concentration of the boron nitride nanosheet reached 10 mg/mL, precipitation would occur due to very high concentration of the nanosheet (see Table 10-Table 11).

TABLE 10

Dispersibility of a Two-Dimensional Boron Nitride Nanosheet in Water (mass ratio of sulfonated polyaniline to boron nitride = 1:1)

| 5 mg/10 mL | 10 mg/10 mL | 30 mg/10 mL | 50 mg/10 mL | 100 mg/10 mL |
|---|---|---|---|---|
| Good without obvious precipitation | Good without obvious precipitation | Good without obvious precipitation | Good without obvious precipitation | With a precipitate |

TABLE 11

Dispersibility of a Two-Dimensional Boron Nitride Nanosheet in Ethanol (mass ratio of sulfonated polyaniline to boron nitride = 1:2)

| 5 mg/10 mL | 10 mg/10 mL | 30 mg/10 mL | 50 mg/10 mL | 100 mg/10 mL |
|---|---|---|---|---|
| Good without obvious precipitation | Good without obvious precipitation | Good without obvious precipitation | Good without obvious precipitation | With a precipitate |

The stable boron nitride nanosheet dispersions obtained in Example 6-Example 8 were dried under vacuum to form boron nitride powders. When these powders were redispersed in the organic solvent, stable dispersion systems can be formed by fierce stirring or ultrasound, and no obvious precipitation phenomena occurred after the dispersion systems were left to stand at room temperature for 30 d or more.

Example 9: Synthesis of Aniline Trimer and Use Thereof in the Exfoliation of a Molybdenum Disulfide Nanosheet Synthesis of aniline trimer: p-phenylenediamine sulfate (8.87 g), and aniline (5.56 g) were added to a hydrochloric acid solution (1M, 500 mL) present in a three-necked flask, and cooled to −5° C. A hydrochloric acid (1M, 150 mL) solution of ammonium persulfate (13.62 g) was slowly dropwise added to the reaction flask through a dropping funnel. On completion of the dropwise addition, the resulting solution was further stirred for additional 1 h. The reaction product was filtered under suction, and washed with a considerable amount of deionized water, to obtain a dark green solid product. Then the product was washed with 10 wt % aqueous ammonia solution, then washed with deionized water twice, and finally dried and kept in a vacuum oven at 40° C. for later use. The resulting aniline trimer has good solubility in solvents, such as ethanol, ethyl acetate, tetrahydrofuran, chloroform, or dimethylformamide.

Figure 8:
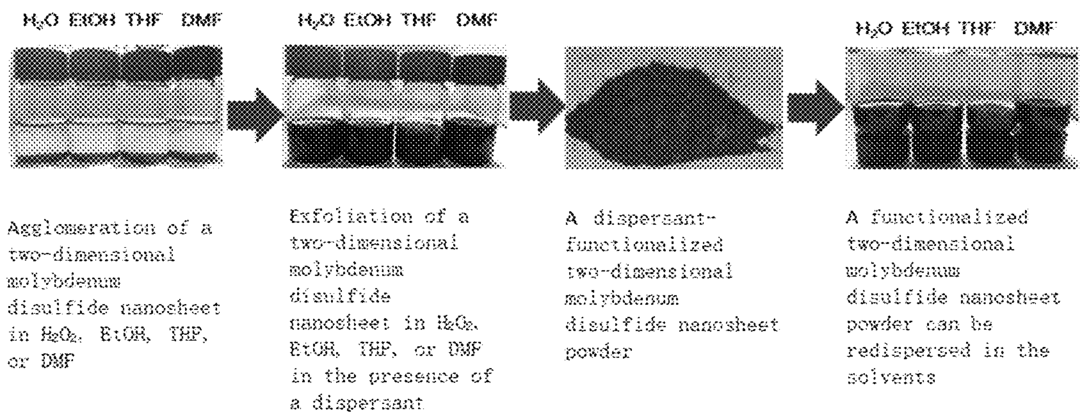
FIG. 8 is photos of dispersion of molybdenum disulfide in the absence of a dispersant and in the presence of a dispersant in example 9 of the present invention.

The aniline trimer obtained in this example and a molybdenum disulfide powder were mixed at a certain ratio, were dissolved in ethanol (EtOH) and tetrahydrofuran (THF) respectively, and ultrasonically dispersed for 10 min, to test the dispersion effect of molybdenum disulfide in the presence of the oligoaniline, as shown in Table 12 and Table 13. When the concentration of a molybdenum disulfide nanosheet was less than 2.5 mg/mL (see FIG. 9 for the appearance of the exfoliated molybdenum disulfide nanosheet), an aniline trimer-molybdenum disulfide complex can form a stable dispersion in ethanol and tetrahydrofuran, and no obvious precipitation occurred; and when the concentration of the molybdenum disulfide nanosheet reached 5 mg/mL, aggregation and precipitation of partial sheets would occur after the dispersion was left to stand for 1 h (see FIG. 8).

TABLE 12

Dispersion Effect of Molybdenum Disulfide in Ethanol in the Presence of Aniline Trimer (molybdenum disulfide:aniline trimer = 1:1)

| 5 mg/10 mL | 15 mg/10 mL | 25 mg/10 mL | 50 mg/10 mL |
|---|---|---|---|
| Good without obvious precipitation | Good without obvious precipitation | Good without obvious precipitation | Good with partial precipitation |

TABLE 13

Dispersion Effect of Molybdenum Disulfide in Tetrahydrofuran in the Presence of Aniline Trimer (molybdenum disulfide:aniline trimer = 1:1)

| 5 mg/10 mL | 15 mg/10 mL | 25 mg/10 mL | 50 mg/10 mL |
|---|---|---|---|
| Good without obvious precipitation | Good without obvious precipitation | Good without obvious precipitation | With partial precipitation |

Example 10: Synthesis of Aniline Tetramer and Use Thereof in the Exfoliation of a Molybdenum Disulfide Nanosheet N-phenyl-p-phenylenediamine (11.08 g, 60 mmol), acetone (300 mL), a hydrochloric acid (1M, 75 mL) solution, and deionized water (300 mL) were successively added a 500 mL round bottom flask, and stirred until fully dissolved. Then a hydrochloric acid solution (1M, 150 mL) of ammonium persulfate (13.6 g, 60 mmol) was gradually added dropwise to the solution. On completion of the dropwise addition, the resulting solution was kept at −5° C. for 3 h. On completion of the reaction, the resulting solution was filtered under suction by a Buchner funnel, then washed with 10 wt % ammonia water, then washed with a considerable amount of deionized water twice, and finally dried and kept in a vacuum oven at 40° C. for later use. The obtained aniline tetramer has good solubility in tetratetrahydrofuran, ethyl acetate, or N,N-dimethylformamide.

The aniline tetramer obtained in this example and a molybdenum disulfide powder were dissolved in THF at a certain ratio, and ultrasonically dispersed for 10 min, to test the dispersion effect thereof in the solvent, as shown in Table 14. When the concentration of a molybdenum disulfide nanosheet was less than 2.5 mg/mL, an aniline tetramer-molybdenum disulfide complex can form a stable dispersion in tetrahydrofuran, and no obvious precipitation occurred; and when the concentration of the molybdenum disulfide nanosheet reached 5 mg/mL, partial aggregation and precipitation would occur.

TABLE 14

Dispersion Effect of Molybdenum Disulfide in Tetrahydrofuran in the Presence of Aniline Tetramer (molybdenum disulfide:aniline tetramer = 1:1)

| 5 mg/10 mL | 15 mg/10 mL | 25 mg/10 mL | 50 mg/10 mL |
|---|---|---|---|
| Good without obvious precipitation | Good without obvious precipitation | Good without obvious precipitation | With partial precipitation |

Example 11: Synthesis of Carboxyl End-Capped Aniline Trimer and Use Thereof in the Exfoliation of a Molybdenum Disulfide Nanosheet Aniline trimer (2.92 g) was dissolved in 50 mL of THF, then maleic anhydride (2.46 g) was added, the resulting solution was kept at 40° C. for 3 h, and the reaction product was precipitated with petroleum ether, to obtain carboxyl end-capped aniline trimer (4.8 g). Water solutions of weighed carboxylated aniline trimer, 2 molar equivalents of NaOH, and a molybdenum disulfide nanosheet powder (weight ratio of it to the carboxylated aniline trimer=1:1) at different concentrations were prepared, and ultrasonically dispersed for 10 min. The dispersion effect was as shown in Table 15. When the concentration of the molybdenum disulfide nanosheet was less than 2.5 mg/mL, a stable dispersion can be formed, while when the concentration was 5 mg/mL, the molybdenum disulfide nanosheet tended to be saturated in water, and partial precipitation occurred after the dispersion was left to stand for 1 h.

TABLE 15

Dispersion Effect of Molybdenum Disulfide in Water in the Presence of Carboxyl End-capped Aniline Trimer (molybdenum disulfide:carboxyl end-capped aniline trimer = 1:1)

| 5 mg/10 mL | 15 mg/10 mL | 25 mg/10 mL | 50 mg/10 mL |
|---|---|---|---|
| Good without obvious precipitation | Good without obvious precipitation | Good without obvious precipitation | With partial precipitation |

Example 12: Synthesis of Carboxylic Acid End-Capped Aniline Tetramer and Use Thereof in the Exfoliation of a Molybdenum Disulfide Nanosheet Aniline tetramer (2.1 g) was added to 50 mL of THF, then maleic anhydride (0.68 g) was added, and the resulting solution was kept at 40° C. for 3 h, to obtain a carboxyl derivative of aniline tetramer by precipitation with petroleum ether. A water solution of the obtained carboxyl derivative of aniline tetramer, 2 molar equivalents of NaOH, and a molybdenum disulfide powder at a certain concentration was prepared, and ultrasonically processed for 10 min. The dispersion effect was as shown in Table 16. When the concentration of a molybdenum disulfide nanosheet was less than 3 mg/mL, a stable dispersion can be formed, while when the concentration was 5 mg/mL, the molybdenum disulfide nanosheet tended to be saturated in water, and partial precipitation occurred after the dispersion was left to stand for 1 h.

TABLE 16

Dispersion Effect of Molybdenum Disulfide in Water in the Presence of Carboxylic Acid End-capped Aniline Tetramer (molybdenum disulfide:carboxylic acid end-capped aniline tetramer = 1:1)

| 5 mg/10 mL | 15 mg/10 mL | 30 mg/10 mL | 50 mg/10 mL |
|---|---|---|---|
| Good without obvious precipitation | Good without obvious precipitation | Good without obvious precipitation | With partial precipitation |

Example 13: Synthesis of Carboxyl End-Capped Aniline Pentamer and Use Thereof in the Exfoliation of a Molybdenum Disulfide Nanosheet Carboxyl end-capped aniline pentamer used in this example was synthesized according to the reference (Chemical Journal of Chinese Universities, 2004, 9, 1768). A water solution of the obtained carboxyl derivative of aniline pentamer, 2 molar equivalents of NaOH, and a molybdenum disulfide powder at a certain concentration was prepared, and ultrasonically processed for 10 min. The dispersion effect was as shown in Table 17. When the concentration of a molybdenum disulfide nanosheet was less than 2.5 mg/mL, a stable dispersion can be formed, while when the concentration was 5 mg/mL, the molybdenum disulfide nanosheet tended to be saturated in water, and partial precipitation occurred after the dispersion was left to stand for 1 h.

TABLE 17

Dispersion Effect of Molybdenum Disulfide in Water in the Presence of Carboxyl End-capped Aniline Pentamer (molybdenum disulfide:carboxyl end-capped aniline pentamer = 1:1)

| 5 mg/10 mL | 15 mg/10 mL | 25 mg/10 mL | 50 mg/10 mL |
|---|---|---|---|
| Good without obvious precipitation | Good without obvious precipitation | Good without obvious precipitation | With partial precipitation |

Figure 9:
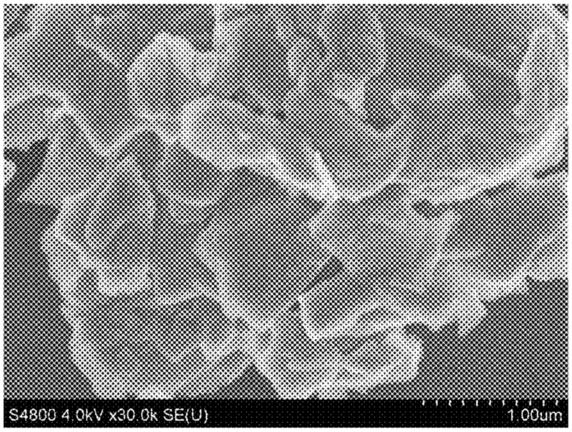
FIG. 9 is a SEM image of an exfoliated molybdenum disulfide nanosheet in example 9 of the present invention.
Figure 10A:
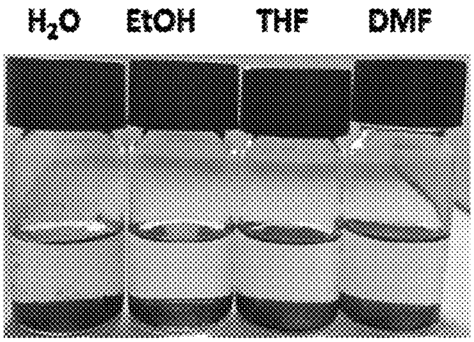
FIG. 10*a*-FIG. 10*b* are photos of dispersion of molybdenum disulfide in the absence of a dispersant and in the presence of a dispersant in example 14 of the present invention.
Figure 10B:
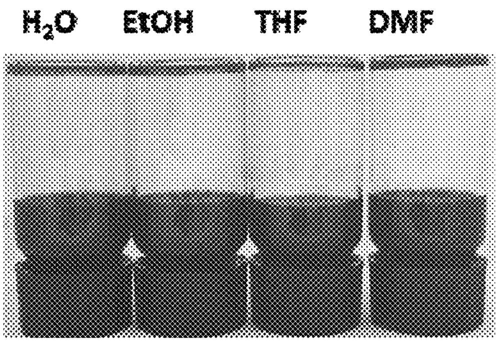

The stable two-dimensional molybdenum disulfide nanosheet dispersions obtained in Example 9-Example 13 were dried under vacuum to form powders (see FIG. 9). When these powders were redispersed in the conventional solvent, stable dispersion systems can be formed by fierce stirring or ultrasound (see FIG. 8), and substantially no precipitation phenomena occurred after the dispersion systems were left to stand at room temperature for 10 d or more.

Example 14: Synthesis of an Eigenstate Polyaniline and Use Thereof in the Exfoliation of a Two-Dimensional Molybdenum Disulfide Nanosheet in an Organic Solvent Aniline (7 g) was dissolved in 100 mL of 1 M hydrochloric acid present in a 200 mL round bottom flask while stirring, and cooled to 0° C. Then, 17 g of ammonium persulfate was dissolved in 50 mL of a 1M hydrochloric acid solution, and the resulting solution was slowly dropwise added to the round bottom flask. On completion of the dropwise addition, the resulting solution was kept for 12 h, and the reaction solution was filtered, and washed with distilled water twice to obtain a dark green doped polyaniline. The obtained dark green polyaniline was immersed in 10 wt % ammonia water for 12 h, filtered, washed with distilled water until the filtrate was neutral, and dried under vacuum at 65° C. for 24 h, to obtain an eigenstate polyaniline (5.2 g) for later use. The eigenstate polyaniline has good solubility in a strongly polar solvent, such as DMF, or NMP.

Figure 11:
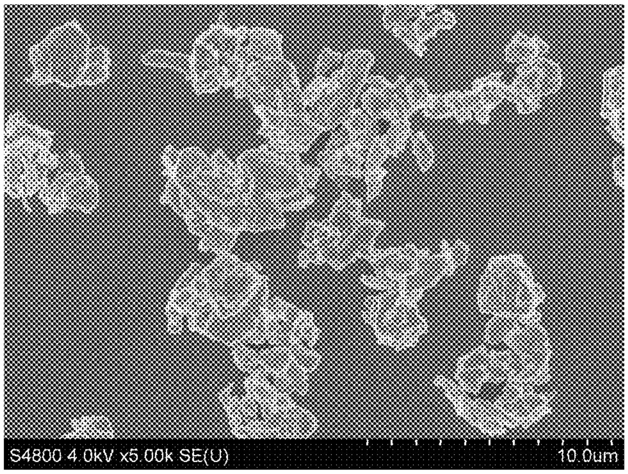
FIG. 11 is a SEM image of an exfoliated molybdenum disulfide nanosheet in example 14 of the present invention.

The eigenstate polyaniline prepared in this example, a molybdenum disulfide powder, and DMF were mixed at a certain ratio, and ultrasonically dispersed for 10 min, to test the dispersion effect of molybdenum disulfide in the presence of the polyaniline. The molybdenum disulfide nanosheet was exfoliated in the presence of the polyaniline (see FIG. 11 for the appearance of the exfoliated molybdenum disulfide nanosheet). When the concentration of the molybdenum disulfide nanosheet was less than 3 mg/mL, a stable dispersion can be formed, and no obvious precipitation occurred after it was left to stand at room temperature for 1 d, while when the concentration of the molybdenum disulfide nanosheet reached 5 mg/mL, partial precipitation would occur (see Table 18).

TABLE 18

Dispersibility of a Two-Dimensional Molybdenum Disulfide Nanosheet in DMF (mass ratio of polyaniline to molybdenum disulfide = 1:1)

| 5 mg/10 mL | 10 mg/10 mL | 30 mg/10 mL | 50 mg/10 mL |
|---|---|---|---|
| Good without obvious precipitation | Good without obvious precipitation | Good without obvious precipitation | With little precipitation |

Example 15: Synthesis of an Alkyl-Substituted Polyaniline and Use Thereof in the Exfoliation of a Two-Dimensional Molybdenum Disulfide Nanosheet isopropylaniline (6.0 g) was dissolved in 100 mL of 1 M hydrochloric acid present in a 200 mL round bottom flask while stirring, and cooled to 0° C. Then, 11.44 g of ammonium persulfate was dissolved in 50 mL of a 1M hydrochloric acid solution, and the resulting solution was slowly dropwise added to the round bottom flask. On completion of the dropwise addition, the resulting solution was kept for 12 h, and the reaction solution was filtered, and washed with distilled water twice to obtain a dark green doped isopropyl-substituted polyaniline. The obtained dark green polyaniline was immersed in 10 wt % ammonia water for 12 h, filtered, washed with distilled water until the filtrate was neutral, and dried under vacuum at 65° C. for 24 h, to obtain an eigenstate isopropyl-substituted polyaniline (4.6 g) for later use. The eigenstate isopropyl polyaniline has good solubility in a polar solvent, such as THF, $CHCl_3$, DMF, or NMP.

The isopropyl polyaniline prepared in this example, a molybdenum disulfide powder, and THF were mixed at a certain ratio, and ultrasonically dispersed for 10 min, to test the dispersion effect of molybdenum disulfide in the presence of the isopropyl-substituted polyaniline. The molybdenum disulfide nanosheet was exfoliated in the presence of the isopropyl-substituted polyaniline. When the concentration of the molybdenum disulfide nanosheet was less than 3 mg/mL, a stable dispersion can be formed, while when the concentration of the molybdenum disulfide nanosheet reached 5 mg/mL, partial precipitation would occur (see Table 19).

TABLE 19

Dispersibility of a Two-Dimensional Molybdenum Disulfide Nanosheet in DMF (mass ratio of polyaniline to molybdenum disulfide = 1:1)

| 5 mg/10 mL | 10 mg/10 mL | 30 mg/10 mL | 50 mg/10 mL |
|---|---|---|---|
| Good without obvious precipitation | Good without obvious precipitation | Good without obvious precipitation | With little precipitation |

Example 16: Synthesis of a Sulfo-Substituted Polyaniline and Use Thereof in the Exfoliation of a Two-Dimensional Molybdenum Disulfide Nanosheet anilinesulfonic acid (4.3 g) and aniline (2.3 g) were dissolved in 250 mL of 1 M hydrochloric acid present in a 200 mL round bottom flask while stirring, and cooled to 0° C. Then, 11.39 g of ammonium persulfate was dissolved in 150 mL of a 1M hydrochloric acid solution, and the resulting solution was slowly dropwise added to the round bottom flask. On completion of the dropwise addition, the resulting solution was kept for 12 h, the reaction solution was centrifuged, and the precipitate was washed with distilled water twice to obtain a dark green sulfonated aniline copolymer for later use. The sulfonated aniline copolymer has good solubility in a solvent, such as $H_2O$, EtOH, THF, DMF, or NMP.

The sulfonated polyaniline prepared in this example, a molybdenum disulfide powder, and water (or ethanol) were mixed at a certain ratio, and ultrasonically dispersed for 10 min, to test the exfoliation and dispersion effect of a molybdenum disulfide nanosheet. The molybdenum disulfide nanosheet was exfoliated in the presence of the sulfonated polyaniline. When the concentration of the molybdenum disulfide nanosheet was less than 3 mg/mL, a stable dispersion can be formed, while when the concentration of the molybdenum disulfide nanosheet reached 5 mg/mL, partial precipitation would occur after the dispersion was left to stand for 1 h (see Table 20-Table 21).

TABLE 20

Dispersibility of a Two-Dimensional Molybdenum Disulfide Nanosheet in Water (mass ratio of sulfonated polyaniline to molybdenum disulfide = 1:1)

| 5 mg/10 mL | 10 mg/10 mL | 30 mg/10 mL | 50 mg/10 mL |
|---|---|---|---|
| Good without obvious precipitation | Good without obvious precipitation | Good without obvious precipitation | With little precipitation |

TABLE 21

Dispersibility of a Two-Dimensional Molybdenum Disulfide Nanosheet in Ethanol (mass ratio of sulfonated polyaniline to molybdenum disulfide = 1:2)

| 5 mg/10 mL | 10 mg/10 mL | 30 mg/10 mL | 50 mg/10 mL |
|---|---|---|---|
| Good without obvious precipitation | Good without obvious precipitation | Good without obvious precipitation | With little precipitation |

The stable two-dimensional molybdenum disulfide nanosheet dispersions obtained in Example 14-Example 16 were dried under vacuum to form molybdenum disulfide powders. When these powders were redispersed in the conventional solvent, stable dispersion systems can be formed by fierce stirring or ultrasound, and substantially no precipitation phenomena occurred after the dispersion systems were left to stand at room temperature for 10 d or more.

It should be noted that the terms “including”, “contain” or any other variants thereof herein are intended to cover non-exclusive inclusiveness, so that the process, method, article or device including a series of elements includes not only those elements, but also other elements that are not clearly enumerated, or further includes inherent elements for this process, method, article or device.

It should be noted that the above description is only specific embodiments of the present invention. For those skilled in the art, they may still make a number of improvements and modifications without departing from the principle of the present disclosure, and such improvements and modifications shall also be regarded as falling within the scope of protection of the present disclosure.

What is claimed is:

1. A method of preparing a dispersion of a two-dimensional nanomaterial by liquid phase exfoliation, the method comprising:

uniformly mixing a two-dimensional nanomaterial with a dispersant in a dispersion medium to form a reaction mixture; and applying at least one ultrasound, stirring, or oscillation to the reaction mixture to disperse the two-dimensional nanomaterial into the dispersion medium in the presence of the dispersant to form a stable dispersion of the two-dimensional nanomaterial, wherein the method further comprises centrifuging the stable dispersion of the two-dimensional nanomaterial to collect a complex of the two-dimensional nanomaterial and the dispersant, and redispersing the complex in the dispersion medium;

wherein the dispersant comprises any one or a combination of two or more of an oligoaniline, an oligoaniline derivative, or a polyaniline conducting polymer, and is capable of binding to the two-dimensional nanomaterial by a physical actin to enable the two-dimensional nanomaterial to be stably dispersed in the dispersion medium; wherein the oligoaniline derivative comprises a carboxyl end-capped oligoaniline derivative, an alkyl-substituted oligoaniline derivative, an oligoaniline binding to a functional group, or an oligoaniline; wherein the functional group comprises any one or a combination of two or more of alkoxy, carboxyl, sulfo, or phosphoryl; and wherein the oligoaniline derivative is selected from an oligoaniline graft or block polymer wherein the two-dimensional nanomaterial is a two-dimensional boron nitride powder or a two-dimensional molybdenum disulfide powder; and wherein the dispersion medium comprising any one or a combination of two or more of water, an organic solvent, a polymer resin, or a water solution.

2. The method of claim 1, wherein the dispersion medium is an organic solvent selected from any one or a combination of two or more of ethanol, tetrahydrofuran, N,N-dimethylformamide, dimethyl sulfoxide, chloroform, and N-methylpyrrolidone.

3. The method of claim 1, wherein the dispersion medium is selected from water and a water solution.

4. The method of claim 3, wherein the water solution is an alkaline water solution that comprises NaOH, KOH, or ammonia.

5. The method of claim 1, wherein the dispersion medium is an organic solvent selected from at least one of a low boiling solvent and a high boiling polar organic solvent.

6. The method of claim 1, wherein the two-dimensional nanomaterial is in the form of a nanosheet having a thickness of 1-20 nm.

7. The method of claim 1, wherein the dispersant and the two-dimensional nanomaterial have a weight ratio of 0.1-10:1.

8. The method of claim 1, wherein the dispersant and the two-dimensional nanomaterial have a weight ratio of 0.2-2:1.

9. The method of claim 1, wherein the oligoaniline derivative has any one of following chemical formulas:

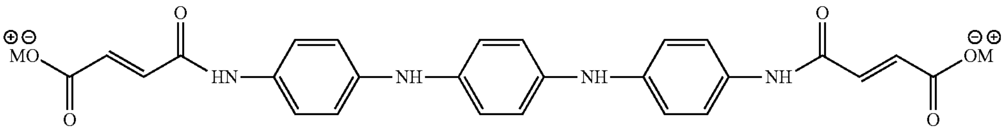

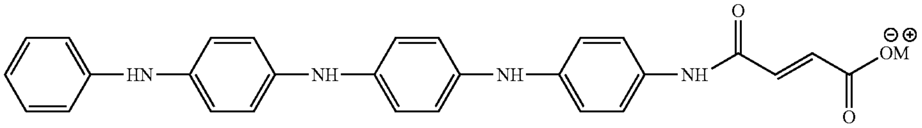

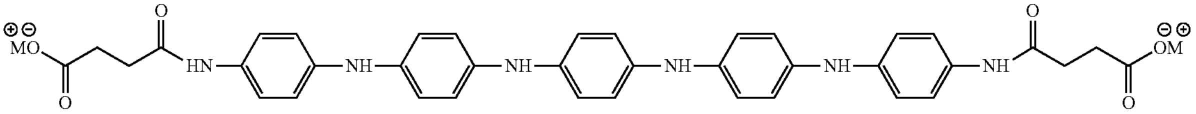

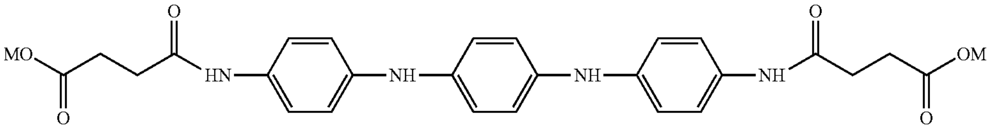

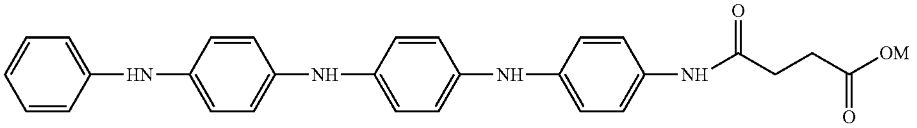

wherein M comprises $H^+$, $Na^+$, $K^+$or a quaternary ammonium salt cation.

10. The method of claim 1, wherein the oligoaniline comprises any one or a combination of two or more of an aniline trimer, an aniline tetramer, an aniline pentamer, or an aniline hexamer.

11. The method of claim 1, wherein the oligoaniline derivative comprises a derivative of any one of an aniline trimer, an aniline tetramer, an aniline pentamer, or an aniline hexamer.

12. The method of claim 1, wherein the polyaniline conducting polymer comprises any one or a combination of two or more of an eigenstate polyaniline, a doped polyaniline, a substituted polyaniline, an oil soluble polyaniline, or a water soluble polyaniline.

13. The method of claim 1, wherein the polyaniline conducting polymer comprises a polyaniline conducting polymer having a structural unit represented by any one of chemical formulas (1)-(3):

(1)

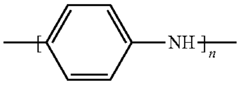

(2)

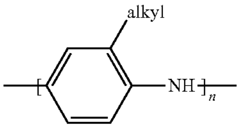

(3)

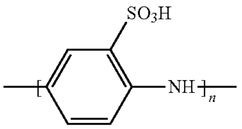

wherein, n=3-500.

* * * * *